(12) United States Patent
Modgil et al.

(10) Patent No.: US 11,238,585 B2
(45) Date of Patent: Feb. 1, 2022

(54) METHOD AND APPARATUS FOR SPECTRAL COMPUTED TOMOGRAPHY (CT) WITH MULTI-MATERIAL DECOMPOSITION INTO THREE OR MORE MATERIAL COMPONENTS

(71) Applicants: The University of Chicago, Chicago, IL (US); CANON MEDICAL SYSTEMS CORPORATION, Otawara (JP)

(72) Inventors: Dimple Modgil, Chicago, IL (US); Patrick La Riviere, Chicago, IL (US); Yan Liu, Vernon Hills, IL (US); Zhou Yu, Vernon Hills, IL (US)

(73) Assignees: The University of Chicago, Chicago, IL (US); CANON MEDICAL SYSTEMS CORPORATION, Otawara (JP)

( * ) Notice: Subject to any disclaimer, the term of this patent is extended or adjusted under 35 U.S.C. 154(b) by 110 days.

(21) Appl. No.: 16/839,733

(22) Filed: Apr. 3, 2020

(65) Prior Publication Data
US 2021/0312612 A1    Oct. 7, 2021

(51) Int. Cl.
*G06T 7/00* (2017.01)
*A61B 6/03* (2006.01)

(52) U.S. Cl.
CPC ............. *G06T 7/0012* (2013.01); *A61B 6/03* (2013.01); *G06T 2207/10072* (2013.01)

(58) Field of Classification Search
CPC ......... G06T 7/0012; G06T 2207/10081; G06T 11/008; G06T 2207/30004; G06T 7/11; A61B 6/032; A61B 6/03; G01N 23/046
See application file for complete search history.

(56) References Cited

U.S. PATENT DOCUMENTS

| 8,290,232 | B2 * | 10/2012 | Liu | A61B 6/032 382/131 |
| 8,855,385 | B2 * | 10/2014 | Kriston | A61B 6/12 382/128 |

(Continued)

OTHER PUBLICATIONS

Mendonca PR, Lamb P, Sahani DV. A Flexible Method for Multi-Material Decomposition of Dual-Energy CT Images. IEEE Trans Med Imaging. Jan. 2014;33(1):99-116. (Year: 2014).*

(Continued)

*Primary Examiner* — Gandhi Thirugnanam
(74) *Attorney, Agent, or Firm* — Oblon, McClelland, Maier & Neustadt, L.L.P.

(57) ABSTRACT

A method and apparatus uses multi-material decomposition of three or more material components to generate material-component images from spectral images reconstructed from spectral computed tomography data. In three-component material decomposition e.g., the Mendonça method is used for multi-material decomposition when the attenuation values satisfy an assumed volume fraction condition (i.e., for a given voxel, the attenuation values are within a triangle having vertices given by unit volume fractions of three respective material components). However, when the volume fraction condition fails (e.g., the attenuation values are outside the triangle), either a shortest-Hausdorff-distance method or a closest-edge method is used for multi-material decomposition. For example, the attenuation values of the voxel are projected onto a lower-dimensional space (e.g., the space of a closest edge) and decomposed into a pair/single material component(s) of the lower-dimensional space.

20 Claims, 11 Drawing Sheets

(56) References Cited

U.S. PATENT DOCUMENTS

| | | | | |
|---|---|---|---|---|
| 8,965,095 | B2* | 2/2015 | Zou | A61B 6/5258 |
| | | | | 382/131 |
| 9,036,879 | B2* | 5/2015 | Mendonca | A61B 6/482 |
| | | | | 382/131 |
| 2007/0217570 | A1* | 9/2007 | Grasruck | A61B 6/405 |
| | | | | 378/53 |
| 2009/0129673 | A1 | 5/2009 | Simon et al. | |
| 2009/0208084 | A1* | 8/2009 | Liu | A61B 6/4014 |
| | | | | 382/131 |
| 2010/0135453 | A1* | 6/2010 | Mendonca | A61B 6/4241 |
| | | | | 378/5 |
| 2011/0216951 | A1* | 9/2011 | Ye | G06T 7/0012 |
| | | | | 382/128 |
| 2014/0010427 | A1* | 1/2014 | Kriston | A61B 6/481 |
| | | | | 382/131 |
| 2014/0050378 | A1* | 2/2014 | Sengupta | G01N 23/046 |
| | | | | 382/131 |
| 2016/0262709 | A1* | 9/2016 | Siewerdsen | A61B 6/032 |
| 2019/0069865 | A1* | 3/2019 | Goshen | A61B 6/032 |
| 2019/0259159 | A1* | 8/2019 | Udupa | A61B 6/5217 |
| 2020/0098468 | A1* | 3/2020 | Gotman | H04N 19/51 |

OTHER PUBLICATIONS

Xi Yue, Ruoshi Ruan, Xiuhua Hu, Yu Kuang, Jing Wang, Yong Long, Tianye Niu. "Statistical image-domain multi-material decomposition for dual energy CT." Med Phys. Author Manuscript; available in PMC Mar. 1, 2018.

Fazel Mirzaei, MSc and Reza Faghihi, PhD. "Quantification of contrast agent materials using a new image-domain multimaterial decomposition algorithm based on dual energy CT." The British Institute of Radiology. Apr. 30, 2019.

* cited by examiner

METHOD AND APPARATUS FOR SPECTRAL COMPUTED TOMOGRAPHY (CT) WITH MULTI-MATERIAL DECOMPOSITION INTO THREE OR MORE MATERIAL COMPONENTS

FIELD

This disclosure relates to reconstructing images in computed tomography (CT) using material decomposition, and, more particularly, to multi-material decomposition into three or more components.

BACKGROUND

Computed tomography (CT) systems and methods are widely used, particularly for medical imaging and diagnosis. CT systems generally create images of one or more sectional slices through a subject's body. A radiation source, such as an X-ray source, irradiates the body from one side. At least one detector on the opposite side of the body receives radiation transmitted through the body. The attenuation of the radiation that has passed through the body is measured by processing electrical signals received from the detector.

A CT sinogram indicates attenuation through the body as a function of position along a detector array and as a function of the projection angle of the X-ray source and the detector array relative to the body. In a sinogram, the spatial dimensions refer to the position along the array of X-ray detectors. The time/angle dimension refers to the projection angle of X-rays, which changes as a function of time during a CT scan. The attenuation resulting from a portion of the imaged object (e.g., a vertebra) will trace out a sine wave around the vertical axis. Those portions farther from the axis of rotation correspond to sine waves with larger amplitudes, and the phases of the sine waves correspond to the angular positions of objects around the rotation axis. Performing an inverse Radon transform—or any other image reconstruction method—reconstructs an image from the projection data represented by the sinogram.

Spectral CT can be realized, e.g., when X-rays having various energies traverse a patient, are then detected using an energy-resolving detector, and reconstructed images are generated from the projection data representing the detected X-ray intensities/attenuation. For example, the respective reconstructed images can correspond to the energy bins of the energy-resolving detectors.

Alternatively, the energy-resolved projection data can be decomposed into material components corresponding to high-Z atoms and low-Z atoms. The reconstructed images can then be generated for the material-component sinograms. Often, the two material components can be a bone component and a water component, wherein the water component includes tissues and fluids primarily composed of water (e.g. blood and soft tissue).

Material decomposition can be achieved using various types of CT scanner configurations capable of determining the spectral differences in the X-ray attenuation, including: using energy integrating detectors in combination with an X-ray source that can selectively generate different X-ray spectra, or using a broad bandwidth X-ray source in combination with a detector that selectively detects different X-ray energy bands. For example, the photon-counting detectors differentiate between the X-rays having different energies by resolving detected X-rays into energy bins and counting the number of X-rays in each of the bins along each detector element of the detector array.

Because different materials (i.e., materials having high-Z atoms and low-Z atoms, respectively) exhibit different spectral attenuation signatures for X-rays, spectral-CT projection data can be decomposed into material components using a material-decomposition method. Material decomposition can be performed in either the sinogram domain or the image domain. Each domain has its respective advantages and drawbacks for material decomposition.

Generally, material decomposition is limited to decomposing projection data or images into two material components because there are only two dominant processes—Compton scattering and Photoelectric attenuation—that determine the spectral attenuation signatures of different materials. However, additional constraints/assumptions, such as a volume fraction constraint, can be imposed enabling material decomposition into more than two unique material components, such as in the Mendonça method. These multi-material decomposition methods fail, however, when the spectral projection data violate these additional constraints/assumptions. Therefore, improved methods are desired that provide multi-material decomposition and are robust to violations of the additional constraints/assumptions.

BRIEF DESCRIPTION OF THE DRAWINGS

A more complete understanding of this disclosure is provided by reference to the following detailed description when considered in connection with the accompanying drawings, wherein.

DETAILED DESCRIPTION

The Mendonça method of multi-material decomposition is described in P. Mendonça et al., "A Flexible Method for Multi-Material Decomposition of Dual-Energy CT Images," IEEE Trans. Med. Imag., 33, pp. 99-116 (2014) and in U.S. Pat. No. 9,036,879, which are both incorporated herein by reference in their entirety. The Mendonça method imposes a volume fraction condition/constraint to uniquely decompose voxel attenuation values from duel energy (DE) computed tomography (CT) images or spectral CT images into three material components. However, when the volume fraction condition is not valid, the Mendonça method breaks down. Accordingly, more robust methods of multi-material decomposition are desired.

The methods and apparatus described herein provide more robust multi-material decomposition. For example, when the volume fraction condition is valid, the Mendonça method is used for multi-material decomposition. When, however, the volume fraction condition is not valid either a shortest-Hausdorff approach or a closest-edge approach is used to determine the material decomposition. In the shortest-Hausdorff approach, a tuple of material components is selected based on a shortest-Hausdorff distance criterion, and the material decomposition is performed using the material components of closest edge from the selected tuple. In the closest-edge approach, the tuple of material components is selected based on which edge is closest in an attenuation-energy space, and the material decomposition is performed using the selected tuple. Additional details for both approaches are described below.

Figure 1:
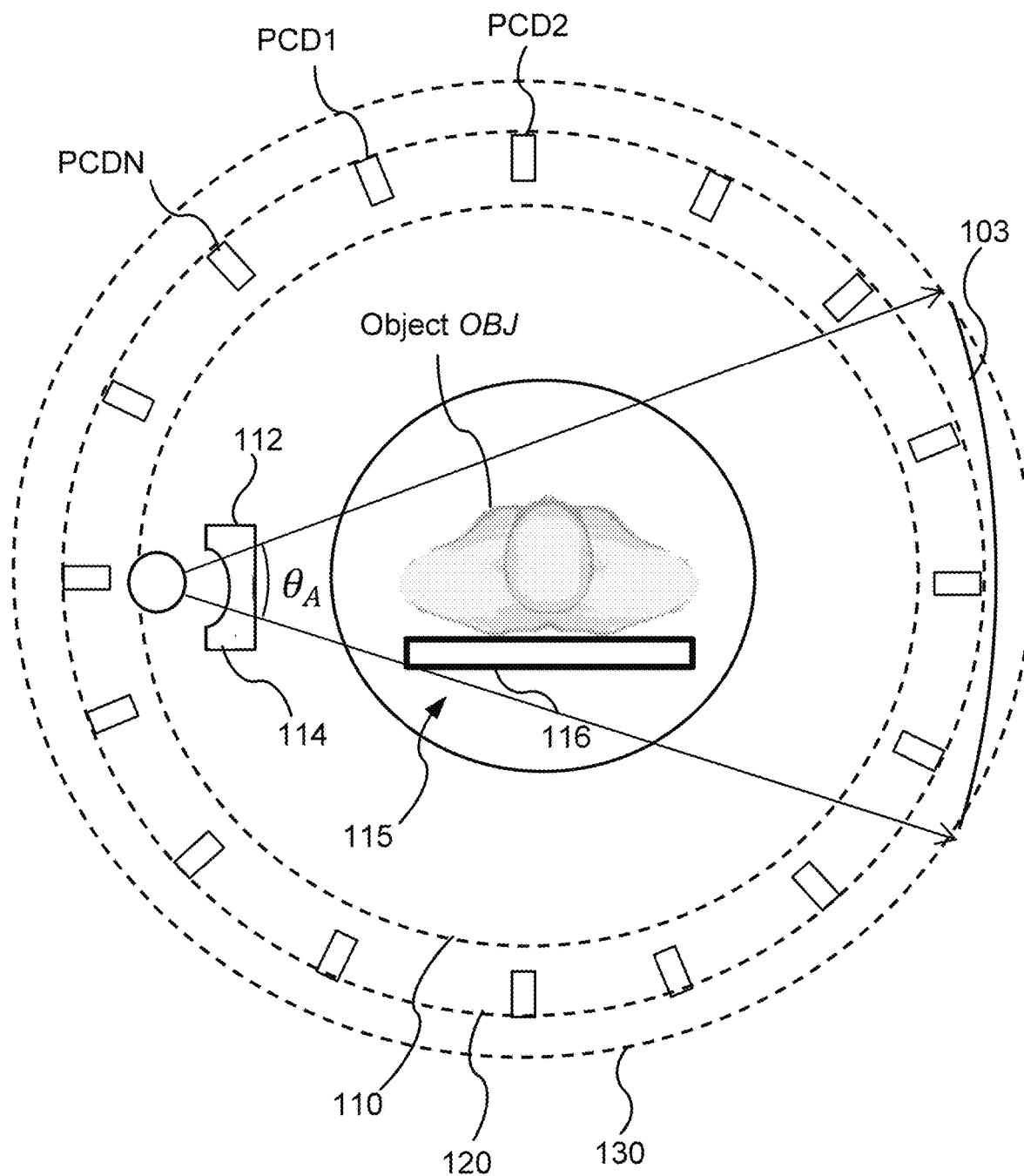
FIG. 1 shows a schematic of an implementation of an arrangement of an X-ray source and X-ray detectors for a CT scanner, according to one implementation.

Referring now to the drawings, wherein like reference numerals designate identical or corresponding parts throughout the several views, FIG. 1 shows source and detector portions of a computed tomography (CT) scanner having both energy-integrating detectors arranged in a third-generation geometry and photon-counting detectors arranged in a fourth-generation geometry. This is just one non-limiting example of a CT scanner configuration that can be used to acquire spectral CT data and reconstruct respective energy-component images, which can then be used for the multi-material decomposition methods described herein. Illustrated in FIG. 1 is an implementation for placing the photon-counting detectors (PCDs) in a predetermined fourth-generation geometry in combination with a detector unit 103 in a predetermined third-generation geometry in a CT scanner system. The diagram illustrates relative positions among an object OBJ to be scanned resting on a table 116, an X-ray source 112, a collimator/filter 114, an X-ray detector 103, and photon-counting detectors PCD1 through PCDN.

In one implementation, the X-ray source 112, the collimator/filter 114 are fixedly connected to a rotational component 110 that is rotatably connected to a gantry, and the PCDs are fixedly connected to a circular component 120 that is fixedly connected to the gantry. The gantry of the CT scanner also includes an open aperture 115 enabling the object OBJ to be placed in a projection plane of the X-rays from the X-ray source. The X-ray detector 103 is fixedly connected to a rotational component 130 that is rotatably connected to the gantry. The rotational component 120 and the rotational component 130 can rotate in unison maintaining the X-ray detector 103 diametrical opposed to the X-ray source 112 to obtain projection data of the object OBJ at a progression of projection angles. Sinograms are created by arranging the projection data with projection angles arranged along one axis and the spatial dimensions of the projection data arranged along the other axes.

This non-limiting example is one option for generating spectral CT projection data. Other options can include using PCDs in a third-generation geometry without any detectors in the fourth-generation geometry. Additionally, the energy-integrating detectors arranged in the third-generation geometry can be used with a dual energy source (e.g., a fast kVp switching source) to generate spectral CT data without using PCDs. Several other variations of spectral CT gantry configurations can be used, as would be understood by a person of ordinary skill in the art.

In spectral CT, radiation having multiple energy components is used to make projective measurements of the object OBJ. These projective measurements are made at a series of angles enabling conventional CT image reconstruction methods similar to non-spectral CT. However, unlike non-spectral CT, spectral CT generates additional information (i.e., spectral attenuation information) enabling a decomposition of the reconstructed spectral images into material components, usually two material components. The material decomposition results in two component materials because there are two dominant interaction mechanisms causing the attenuation of the X-ray beams traversing the imaged object OBJ. These interaction mechanisms are Compton scattering and photoelectric absorption. Mapping the projection data from the spectral domain to the material domain can be performed either before or after the image reconstruction process.

The attenuation of X-rays in biological materials is dominated by two physical processes (i.e., photoelectric absorption and Compton scattering). Thus, the attenuation value corresponding to a given voxel can be expressed as a function of energy, which can be approximated by the decomposition $$\mu(E,x,y) = \mu_{PE}(E,x,y) + \mu_C(E,x,y),$$

wherein $\mu_{PE}(E,x,y)$ is the photoelectric attenuation and $\mu_C(E,x,y)$ is the Compton attenuation. Alternatively, this attenuation coefficient can be rearranged into a decomposition of a high-Z material (i.e., material 1) and a low-Z material (i.e., material 2) to become $$\mu(E,x,y) \approx \mu_1(E)c_1(x,y) + \mu_2(E)c_2(x,y),$$

wherein $c_1(x,y)$ and $c_2(x,y)$ are, respectively correspond to a first and second material component.

Figure 2A:
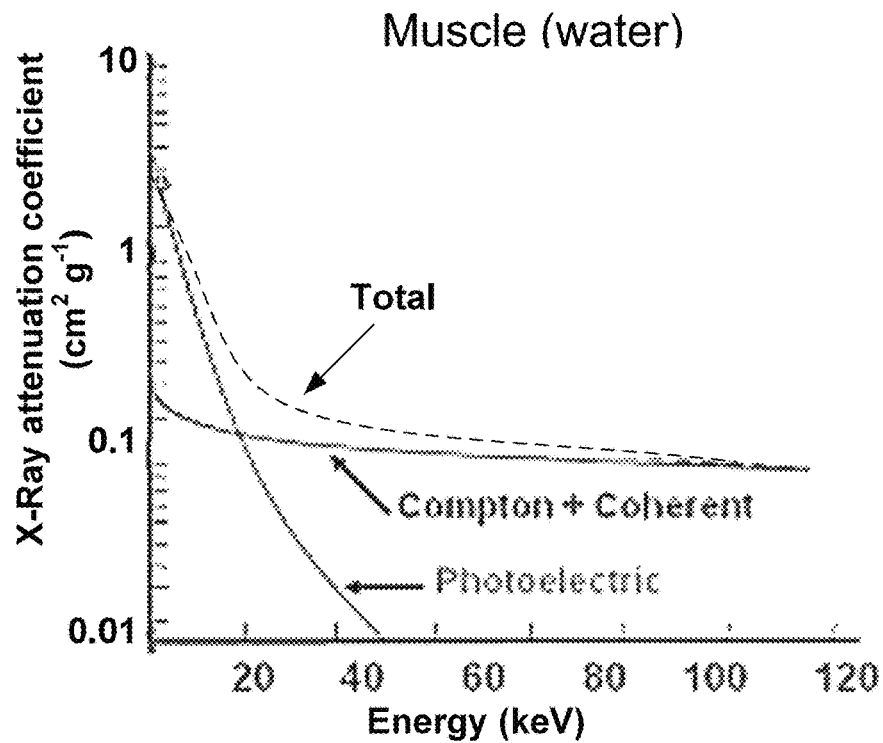
FIG. 2A shows a plot of the Compton and photoelectric contributions to X-ray attenuation in water as a function of the X-ray energy.
Figure 2B:
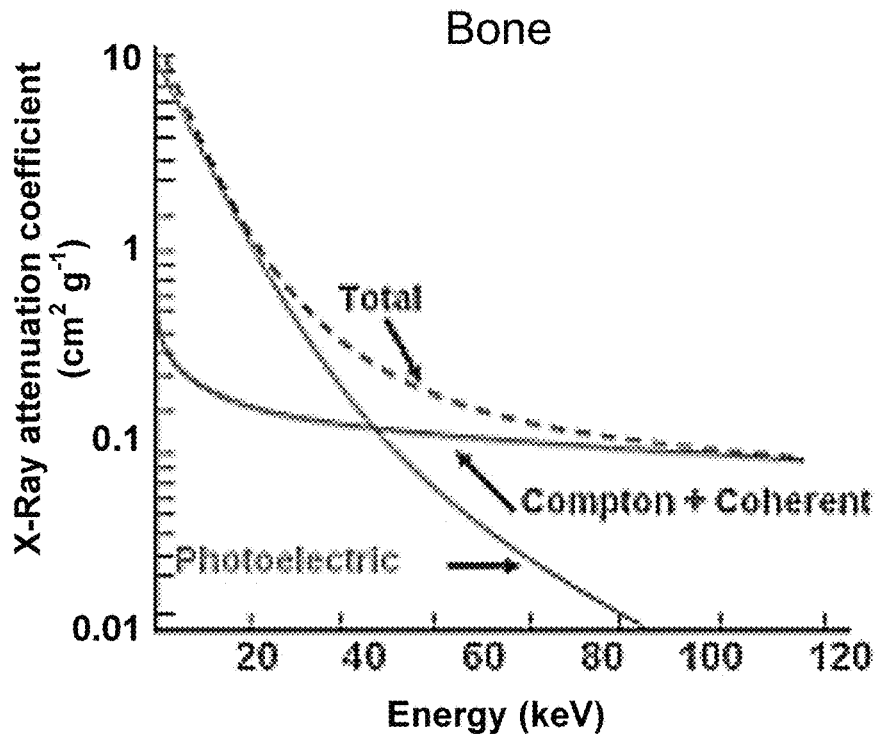
FIG. 2B shows a plot of the Compton and photoelectric contributions to X-ray attenuation in bone as a function of the X-ray energy.

FIGS. 2A and 2B show examples of absorption coefficients $\mu_1(E)$ and $\mu_2(E)$ for muscle (water) and bone respectively.

The detected spectrum is given by $$S(E_i) = S_{air}(E_i) \exp[-\mu_1(E_i)L_1 - \mu_2(E_i)L_2],$$

wherein the attenuation coefficients $\mu_1$ and $\mu_2$ are known functions of the X-ray energy, and the spectrum $S_{air}$, which correspond to the X-rays propagating through air in the absence of an absorptive object OBJ, is also known based on previous calibrations, for example. This detected spectrum can be coarse grained into X-ray energy bins (e.g., five energy bins can be used, each covering a respective energy sub-band, such that combined the energy bins span an energy spectrum from approximately 20 keV to approximately 160 keV). The count value $N_m$ of the $m^{th}$ energy bin can be given by $$N_m = \int dE\, w_m(E) S(E),$$

wherein $w_m(E)$ is a windowing function corresponding to the energy sub-band of the $m^{th}$ energy bin.

For each energy bin/component, a respective CT image can be reconstructed from the projection data corresponding to that energy bin/component. Any known method of image reconstruction can be used. For example, the image reconstruction process can be performed using any of a filtered back-projection method, iterative image reconstruction methods (e.g., using a total variation minimization regularization term), a Fourier-based reconstruction method, or stochastic image reconstruction methods.

When at least two different energy-component images are reconstructed, the attenuation values of the voxels can be decomposed into material components. The term "voxel" refers it a volume pixel. For example, $\mu_{i,j} = \mu(\vec{r}_j, E_i)$ is the attenuation of the $i^{th}$ energy component and the $j^{th}$ voxel at location $\vec{r}_j$. The attenuation values for the first and second material component are given by $\mu_i^{(1)} = \mu^{(1)}(E_i)$ and $\mu_i^{(2)} = \mu^{(2)}(E_i)$, respectively. These attenuation values are scaled to correspond to a unit volume fraction of the respective material component (i.e., the amount of attenuation when the entire volume of the voxel is filled with the material component), and when the energy component is distributed over a range of energy values the unit volume fraction is integrated over the range of energy values (e.g., $\mu_i^{(2)} = \int dE\, w_i(E) \mu^{(2)}(E)$, wherein $w_i(E)$ is a normalized window function representing relative contributions across the range of energy values for the $i^{th}$ energy component.

Using the above nomenclature, the material decomposition can be performed by solving the following matrix equation for the volume fractions $\alpha_i$:

$$\begin{bmatrix} \mu_1^{(1)} & \mu_1^{(2)} \\ \mu_2^{(1)} & \mu_2^{(21)} \end{bmatrix} \begin{bmatrix} \alpha_1 \\ \alpha_2 \end{bmatrix} = \begin{bmatrix} \mu_{1,j} \\ \mu_{2,j} \end{bmatrix},$$

wherein $\alpha_i = V_i / \Sigma_j V_j$ is the fraction of the $i^{th}$ material component, and $\Sigma_j V_j$ is the total volume of the voxel.

In order to decompose the voxel into three material components an additional constraint can be imposed. For example, the volume fractions for three materials can be assumed to add to exactly one (i.e., $\Sigma_{j=1}^3 \alpha_j = 1$). That is, within the volume of the voxel, each part of the volume is occupied by one of the three material components. Then, the above expression can be modified to include three materials, i.e., $$\begin{bmatrix} \mu_1^{(1)} & \mu_1^{(2)} & \mu_1^{(3)} \\ \mu_2^{(1)} & \mu_2^{(2)} & \mu_2^{(3)} \\ 1 & 1 & 1 \end{bmatrix} \begin{bmatrix} \alpha_1 \\ \alpha_2 \\ \alpha_3 \end{bmatrix} = \begin{bmatrix} \mu_{1,j} \\ \mu_{2,j} \\ 1 \end{bmatrix}.$$

Further, it can be assumed that the volume fractions are non-negative and less than or equal to one. To increase the number of material components to four or more, additional constraints can be imposed.

Generally, the volume fraction condition will hold because it is anticipated that the volume fractions will add to one because no part of the volume will be occupied by vacuum (i.e., some material will occupy each part of the volume). For example, in a voxel corresponding to a mixed bone and lung region, the three material components might be air, water, and bone. For a voxel corresponding to a region with a blood vessel that includes a contrast agent (e.g., iodine or gadolinium), different volumes within the voxel will be occupied with water, the contrast agent, or some third component (e.g., fat or bone). By choosing the right triad of material components, generally a linear combination of volume fractions can be found that solves the above matrix equation (i.e., the linear combination adds to one and decomposes the attenuation values $\mu_{1,j}$ of the voxel).

Sometimes, however, there is no triad for which a linear combination of volume fractions solves the above matrix equation, and the volume fraction condition fails. When the volume fraction condition fails, another approach (e.g., the smallest Hausdorff distance approach or the closest edge approach) is used instead.

In the case that the multi-material decomposition is into an n-tuple of three material components (i.e., a 3-tuple), the smallest Hausdorff distance approach is to select, in the attenuation-energy space, the triangle of a 3-tuple (i.e., a triad) of material components that has the smallest Hausdorff distance to the point corresponding to the attenuation values of the voxel. Then, within the selected triangle, a pair of material components corresponding to the edge of the triangle that is closest to the point of the voxel attenuation is used for material decomposition. If a vertex of the triangle is closer than any of the edges, the material decomposition is that the voxel is entirely the material component corresponding to the closest vertex.

The closest edge approach is like the smallest Hausdorff distance approach, except rather than using the triangle with the smallest Hausdorff distance, the closest edge is selected from all of the triangles corresponding to respective triads of material components.

Figure 3A:
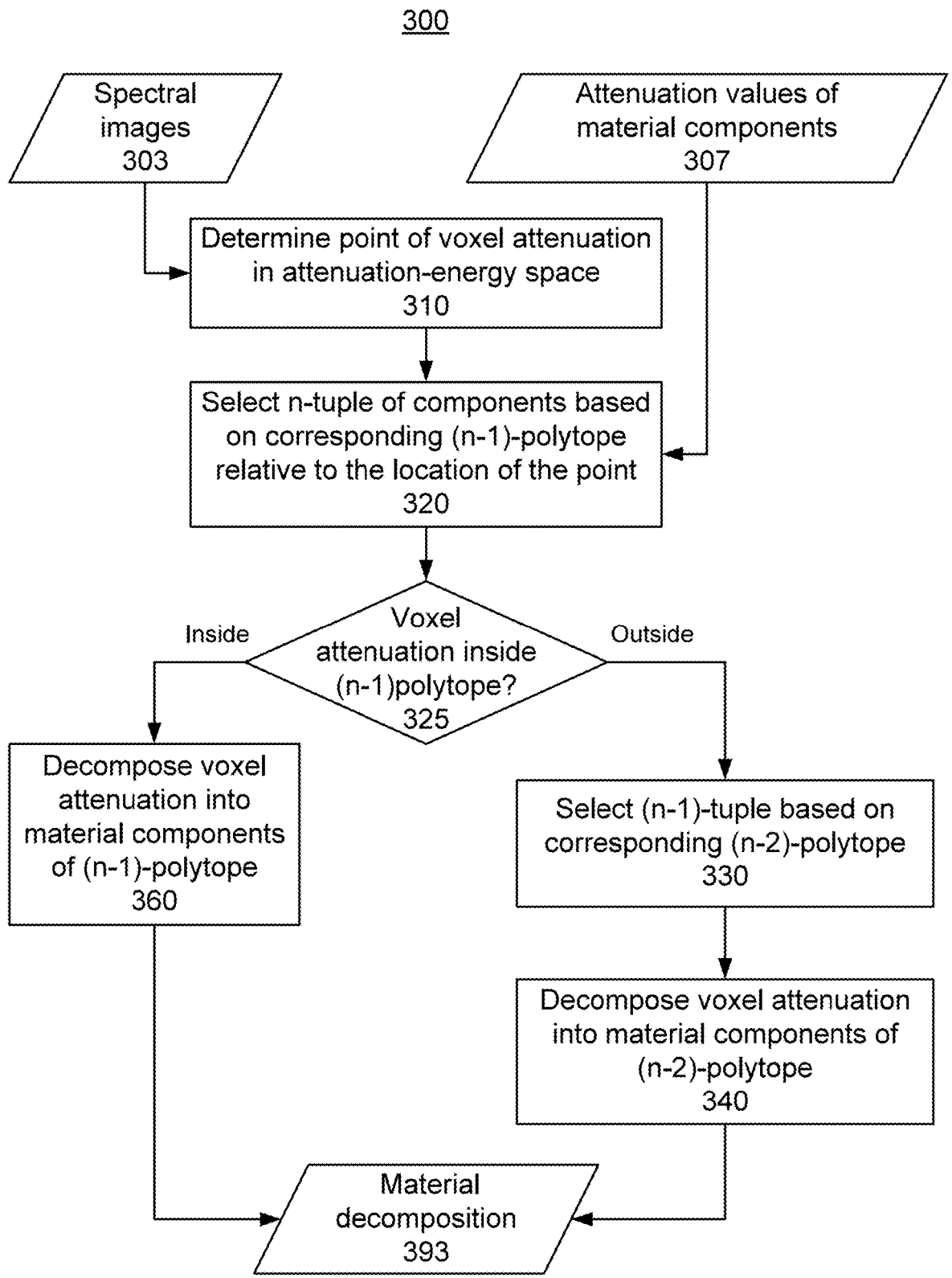
FIG. 3A shows a flow diagram of a robust multi-material decomposition method for any number of material components greater than two, according to one implementation.
Figure 3B:
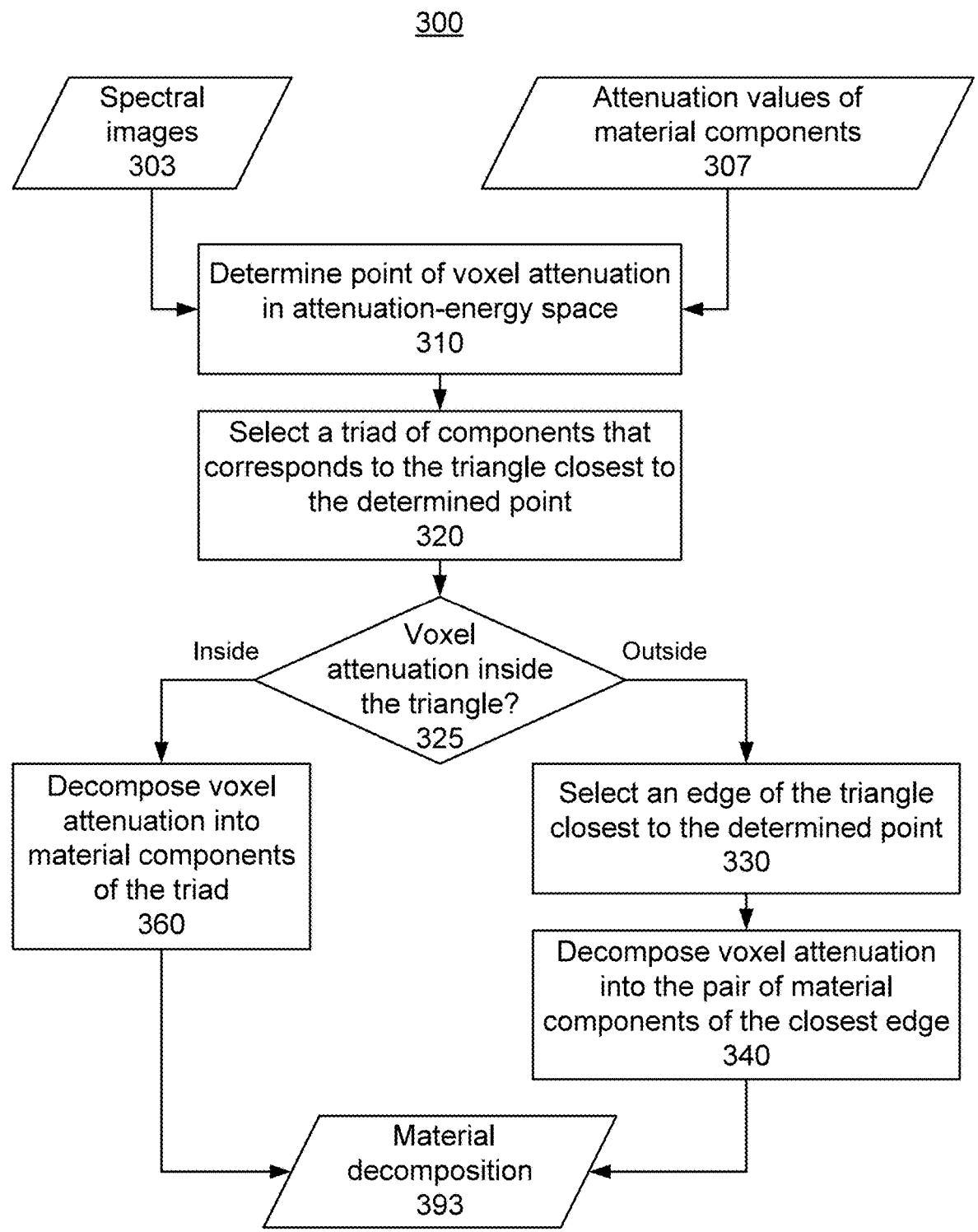
FIG. 3B shows a flow diagram of the robust multi-material decomposition method for three materials, according to one implementation.

FIGS. 3A and 3B show flow diagrams of a method 300 for performing a multi-material decomposition. In FIG. 3A, the method is generalized to decompose the spectral images into a number n of material components, whereas, in FIG. 3B, the number n of material components is three, allowing for a simplified explanation. Method 300 is described for a given voxel within the spectral images 303. That is, performing the steps of method 300 on a given voxel will decompose the energy-component attenuation values of the given voxel into material-component attenuation values. Repeating the illustrated steps for each voxel in the spectral images 303 to decompose the spectral images 303 into material-component images.

In step 310 of method 300, for a given voxel of the spectral images 303, the attenuation values for respective energy components are used to determine a point in the attenuation-energy space. FIGS. 4A-4D illustrate the attenuation-energy space with the attenuation value $\mu(E_1)$ for a first energy component along the horizontal axis and the attenuation value $\mu(E_2)$ for a second energy component along the vertical axis. In the non-limiting example illustrated in FIGS. 4A-4D, a first axis corresponds to the measured attenuation $\mu(E_1)$ of a first material component, and a second axis corresponds to the measured attenuation $\mu(E_2)$ of a second material component.

For example, when the spectral CT data are acquired using kVp switching, the first energy component can be the X-ray spectrum when a low kVp setting is applied to the X-ray tube, and the second energy component can be the X-ray spectrum when a high kVp setting is applied to the X-ray tube. When, a PCD is used to acquire the spectral CT data, the first energy component can correspond to a first energy bin of the PCD, and the second energy component can correspond to a second energy bin of the PCD. Further, the acquired spectral CT can be processed to generate monoenergetic spectral images at two discrete energies $E_1$ and $E_2$. For example, in FIG. 4D, simulated attenuation coefficients are shown for monoenergetic spectral images with the first energy component being $E_1=75$ keV and the second energy component being $E_2=135$ keV.

When only two dominant attenuation mechanism contribute to the X-ray attenuation, which is typically the case for low-Z (atomic number) atoms that are found in biological materials, then all non-redundant information from the material spectral attenuation signature can be performed using only two energy components, as discussed above. However, additional spectral information can be obtained for atoms with high-Z atoms due to K-edge effects. Using this additional information more than two energy components can be used for the material decomposition, in which case the attenuation-energy space can have three or more dimensions. In FIGS. 4A-4D, however, the non-limiting case of an attenuation-energy space having only two energy components is used to illustrate the robust multi-material decomposition method.

Figure 4A:
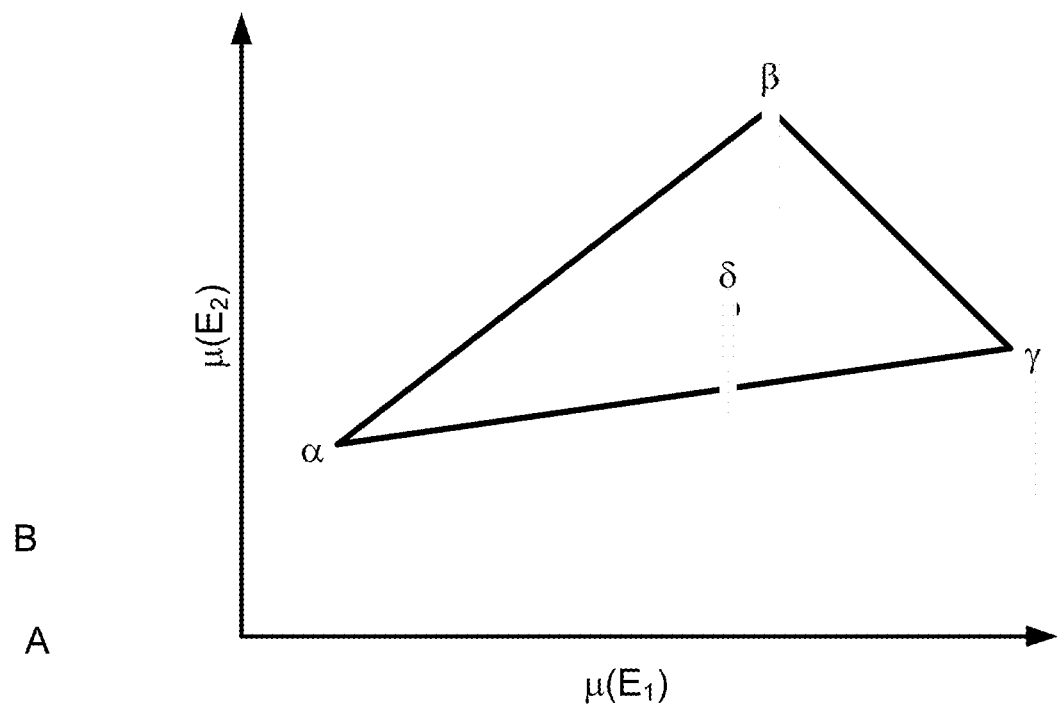
FIG. 4A shows a plot illustrating the multi-material decomposition of a point within a triangle of three material components, according to one implementation.

In FIG. 4A, for example, the attenuation values for a given voxel define a point δ, and unit volume fractions of three material components define respective vertices of a triangle. That is, when the volume corresponding to the voxel is completely filled with the first material, the attenuation corresponding to the first and second material components will have the values indicated by vertex α. Similarly, vertex β corresponds to the attenuation values for a unit volume fraction of the second material, and vertex γ corresponds to the attenuation values for a unit volume fraction of the third material. FIG. 4A shows the case when the point δ is within the triangle Δαβγ, and FIGS. 4B and 4C show two cases when the point δ is outside the triangle Δαβγ.

Figure 4B:
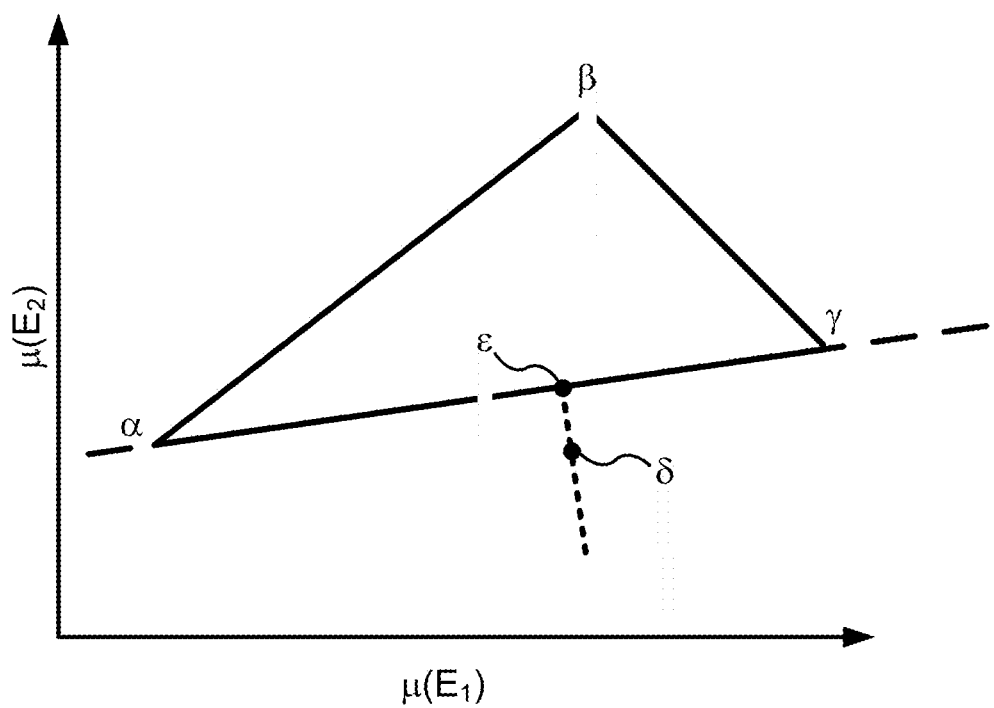
FIG. 4B shows a plot illustrating the multi-material decomposition of a point outside a triangle of the three material components but adjacent to an edge of the triangle, according to one implementation.
Figure 4C:
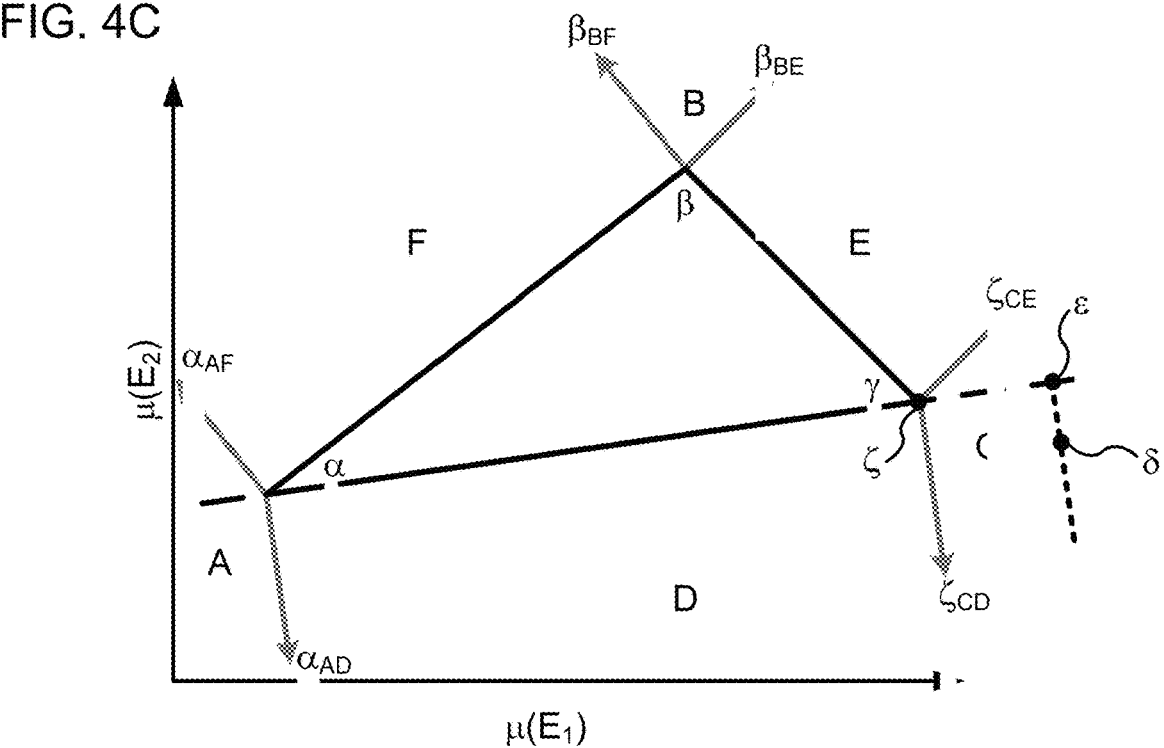
FIG. 4C shows a plot illustrating the multi-material decomposition of a point for which a vertex of the triangle is the closest point in the triangle (i.e., the point outside a triangle of the three material components and is not adjacent to an edge of the triangle), according to one implementation.

For simplicity, FIGS. 4A-4C show only three material components, but generally more than three material components can be used for the multi-material decomposition. When more than three material components can be used for the multi-material decomposition, each set of three (triad) of material components can form a respective triangle. FIG. D shows a non-limiting example of five material components, for example. When the spectral attenuation values of a given voxel are being decomposed into a triad (i.e., an n-tuple in which n=3) of material components and there are four or more material components from which the triad can be selected, the number of possible triads for the decomposition can be as large as the factorial of m−2, wherein m is the total number of material components from which the triad can be selected. Each possible triad of material components corresponds to a respective triangle within the attenuation-energy space. In certain implementations (e.g., the Hausdorff approach), the triad of material components for which the corresponding triangle is closest to the point δ, is selected for the material decomposition.

In step 320 of method 300, a triad (n-tuple) of material components is selected for the material decomposition based on the spatial relation between the point δ and the corresponding triangles ((n-1)-polytopes) of the triads. In certain implementations, the triad corresponding to the triangle with the shortest Hausdorff distance is selected as the triad for the material decomposition.

In another implementation, the triad that both corresponds to the triangle that includes the point δ and that has the smallest area is selected as the triad for the material decomposition. When the point δ is not within any of the triangles, the triangle that both has the smallest area and that includes a point that closest to the point δ is selected as the triad for the material decomposition.

In step 325 of method 300, an inquiry is performed to determine whether the point δ is inside or outside the triangle of the triad selected in step 320. If the point δ is inside the selected triangle ((n-1)-polytope), method 300 proceeds to step 360. Otherwise, method 300 proceeds to step 330. FIG. 4A illustrates the case in which the point δ is inside the triangle, and FIGS. 4B and 4C illustrate cases in which the point δ is outside the triangle.

In step 360 of method 300, the multi-material decomposition is performed to decompose the attenuation values of the voxel into the triad (n-tuple) of material components. For example, the material decomposition can be performed by solving for the volume fractions $\alpha_i$ that satisfy the matrix equation $$\begin{bmatrix} \mu_1^{(1)} & \mu_1^{(2)} & \mu_1^{(3)} \\ \mu_2^{(1)} & \mu_2^{(2)} & \mu_2^{(3)} \\ 1 & 1 & 1 \end{bmatrix} \begin{bmatrix} \alpha_1 \\ \alpha_2 \\ \alpha_3 \end{bmatrix} = \begin{bmatrix} \mu_{1,j} \\ \mu_{2,j} \\ 1 \end{bmatrix},$$

subject to the condition that the volume fractions $\alpha_i$ are non-negative. Other methods of performing the material decomposition into the selected triad of material components can also be used, as would be understood by a person of ordinary skill in the art.

In step 330 of method 300, a pair ((n-1)-tuple) of material components is selected from the triad (n-tuple) of material components that was selected in step 320. This pair ((n-1)-tuple) of material components is selected to correspond to the edge ((n-2)-polytope) of the triangle ((n-1)-polytope) that is closest to the point δ. In FIG. 4B, the edge $\overline{\alpha\gamma}$ is closest to the point δ. The closest edge ((n-2)-polytope) can be determined, e.g., by determining a line (i.e., a n-1 dimensional space) defined by each edge ((n-2)-polytope) of the triangle ((n-1)-polytope) and orthogonally projecting the point δ onto a projected point ε within the line (n-1 dimensional space). The edge ((n-2)-polytope) for which the projected point ε is closest to the point δ is the closest edge ((n-2)-polytope), as shown in FIGS. 4B and 4C.

In step 340 of method 300, the multi-material decomposition is performed to decompose the attenuation values of the voxel into the pair ((n-1)-tuple) of material components from step 330. For example, in FIG. 4B, the volume fraction of the second material component is determined to be zero (i.e., $\alpha_2=0$). Accordingly the material decomposition can be performed by solving for the volume fractions $\alpha_i$ that satisfy the matrix equation $$\begin{bmatrix} \mu_1^{(1)} & \mu_1^{(3)} \\ \mu_2^{(1)} & \mu_2^{(3)} \\ 1 & 1 \end{bmatrix} \begin{bmatrix} \alpha_1 \\ \alpha_3 \end{bmatrix} = \begin{bmatrix} \mu_{1,j}^{(\varepsilon)} \\ \mu_{2,j}^{(\varepsilon)} \\ 1 \end{bmatrix},$$

wherein $\mu_{i,j}^{(\varepsilon)}$ is the attenuation value of the projected point $\varepsilon$ for the $i^{th}$ energy component. subject to the condition that the volume fractions $\alpha_i$ are non-negative.

In FIG. 4C, the projected point $\varepsilon$ is still not within the triangle $\Delta\alpha\beta\gamma$. Thus, a second projection can be performed to determine the closest point ((n-2)-polytope) to the projected point $\varepsilon$ and to the point $\delta$. This point will correspond to a single ((n-1)-tuple) material component. For example, in FIG. 4C the vertex $\gamma$ is closest to the projected point $\varepsilon$ and to the point $\delta$. Thus, the material decomposition would be $\alpha_3=1$.

In certain implementations, the space can be divided up into areas (n-1 dimensional regions): (i) the triangle $\Delta\alpha\beta\gamma$, (ii) area A (which is bounded by the ray $\vec{\alpha}_{AD}$ and ray $\vec{\alpha}_{AF}$), (iii) area B (which is bounded by the ray $\vec{\beta}_{BF}$ and ray $\vec{\beta}_{BE}$), (iv) area C (which is bounded by the ray $\vec{\gamma}_{CE}$ and ray $\vec{\gamma}_{CD}$), (v) area D (which is bounded by the line segment $\overline{\alpha\gamma}$, the ray $\vec{\alpha}_{AD}$, and ray $\vec{\gamma}_{CD}$), (vi) area E (which is bounded by the line segment $\overline{\beta\gamma}$, the ray $\vec{\beta}_{BE}$, and ray $\vec{\gamma}_{CE}$), and (vii) area F (which is bounded by the line segment $\overline{\alpha\beta}$, the ray $\vec{\alpha}_{AF}$, and ray $\vec{\beta}_{BF}$). The rays $\vec{\alpha}_{AF}$ and $\vec{\beta}_{BF}$ are orthogonal to the line segment $\overline{\alpha\beta}$. The rays $\vec{\beta}_{BE}$ and $\vec{\gamma}_{CE}$ are orthogonal to the line segment $\overline{\beta\gamma}$. The rays, the ray $\vec{\alpha}_{AD}$ and $\vec{\gamma}_{CD}$ are orthogonal to the line segment $\overline{\alpha\gamma}$. The material decomposition can depend on which of these seven areas the point $\delta$ is in. When the point $\delta$ is in the triangle $\Delta\alpha\beta\gamma$, material decomposition is performed by decomposing the attenuation into all three material components. When, the point $\delta$ is in the areas A, B, and C, the closest point within the triangle to the point $\delta$ is a vertex. Thus, the material decomposition is performed by decomposing the attenuation into the material component corresponding to the closest vertex. When the point $\delta$ is in the areas E, F, and G, the closest point within the triangle to the point $\delta$ is along one of the three edges. Thus, the material decomposition is performed by decomposing the attenuation into the two material component corresponding to the closest edge. This can be performed, e.g., by orthogonally projecting the point $\delta$ onto the edge, and solving the matrix equation $$\begin{bmatrix} \mu_1^{(1)} & \mu_1^{(3)} \\ \mu_2^{(1)} & \mu_2^{(3)} \\ 1 & 1 \end{bmatrix} \begin{bmatrix} \alpha_1 \\ \alpha_3 \end{bmatrix} = \begin{bmatrix} \mu_{1,j}^{(\varepsilon)} \\ \mu_{2,j}^{(\varepsilon)} \\ 1 \end{bmatrix},$$

as discussed above.

Figure 3C:
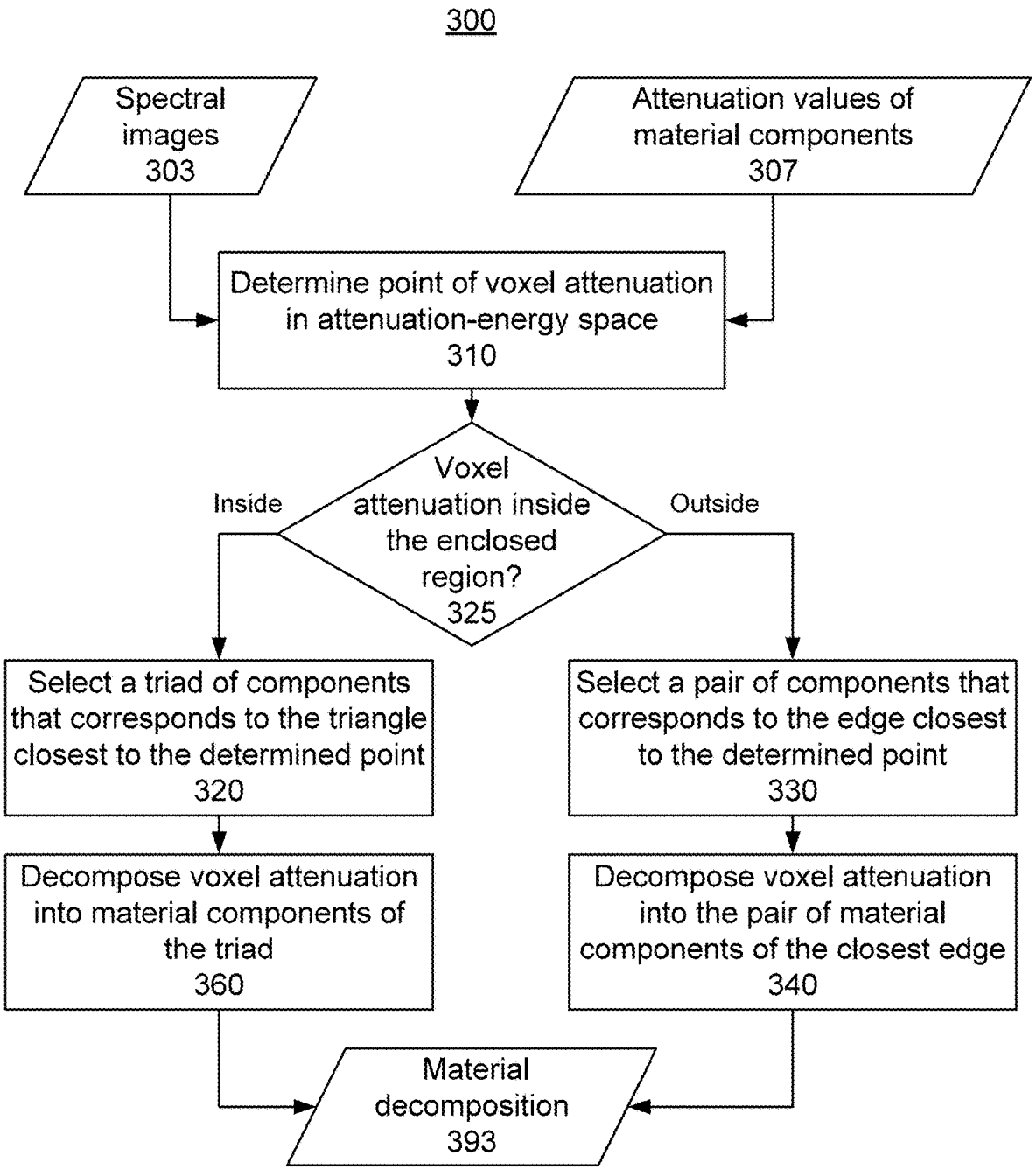
FIG. 3C shows a flow diagram of another implementation of the robust multi-material decomposition method for three material components, according to one implementation.
Figure 3D:
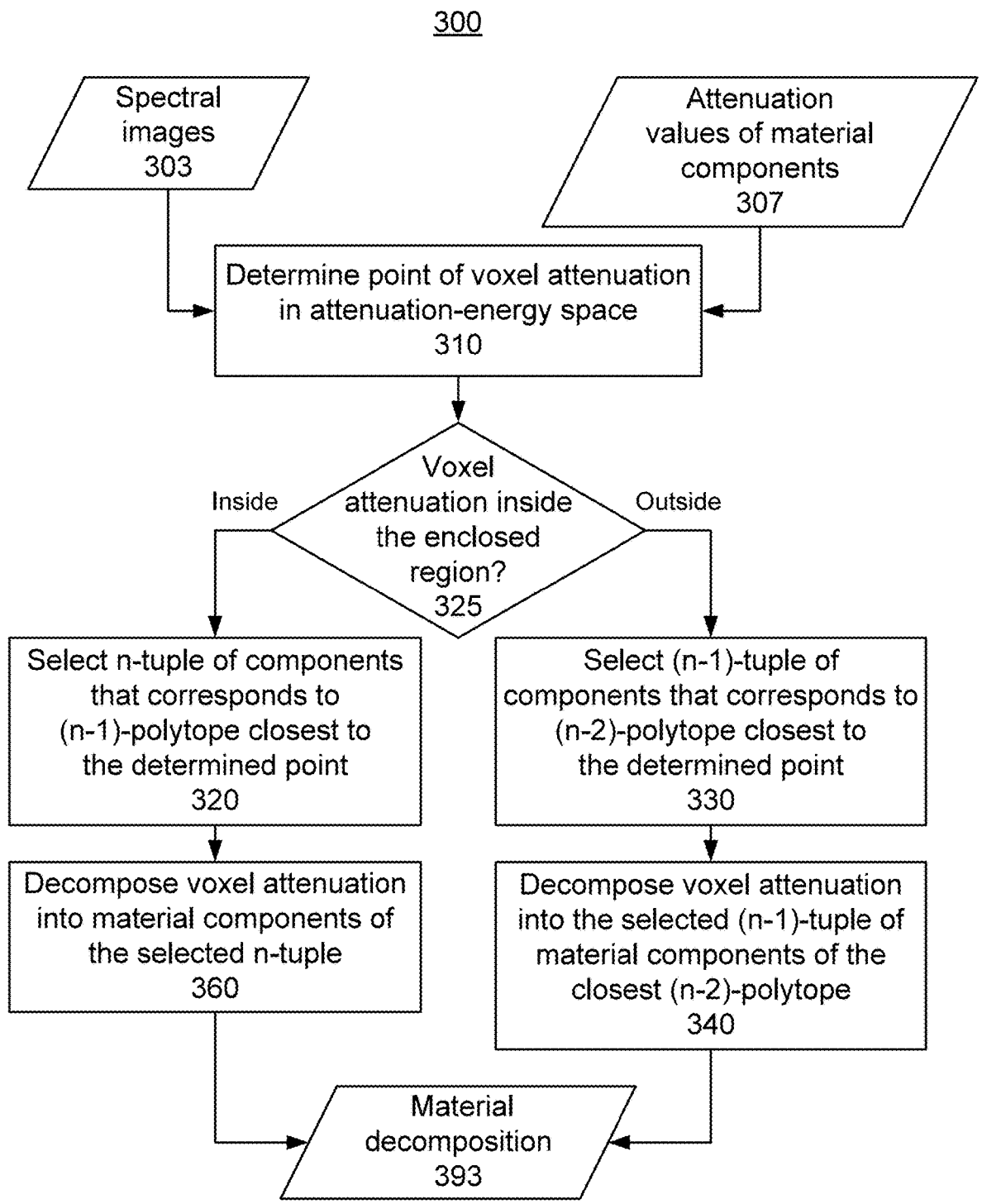
FIG. 3D shows a flow diagram of the another implementation of the robust multi-material decomposition method for any number of material components greater than two, according to one implementation.

FIG. 3C shows an alternative implementation of method 300. In FIG. 3C, step 320 is performed immediately before step 360, rather than being performed immediately before step 325. Further, in step 325, rather than inquiring whether the point $\delta$ is within a particular triangle, the inquiry is whether the point $\delta$ is within the entire region enclosed by the union of all the triangles. If the point $\delta$ is not within the enclosed region of all the triangles, then it will not be within the region of any of the triangles. Therefore, the point $\delta$ will be decomposed into the pair of materials corresponding to a closest edge, or decomposed into the material corresponding to a closest vertex, if the vertex is the closest point to the point $\delta$ within the enclosed region. In this implementation, the choice of whether to look for a closest triangle or edge/vertex can be performed earlier in the method, before determining the closest triangle to point $\delta$. As would be understood by a person of ordinary skill in the art, this implementation of method 300 can be generalized to higher dimensions, similar to how FIG. 3A generalizes to higher dimensions the implementation in FIG. 3B. FIG. 3D illustrates a generalization of the implementation of method 300 in FIG. 3C to arbitrary n greater than two.

Figure 3E:
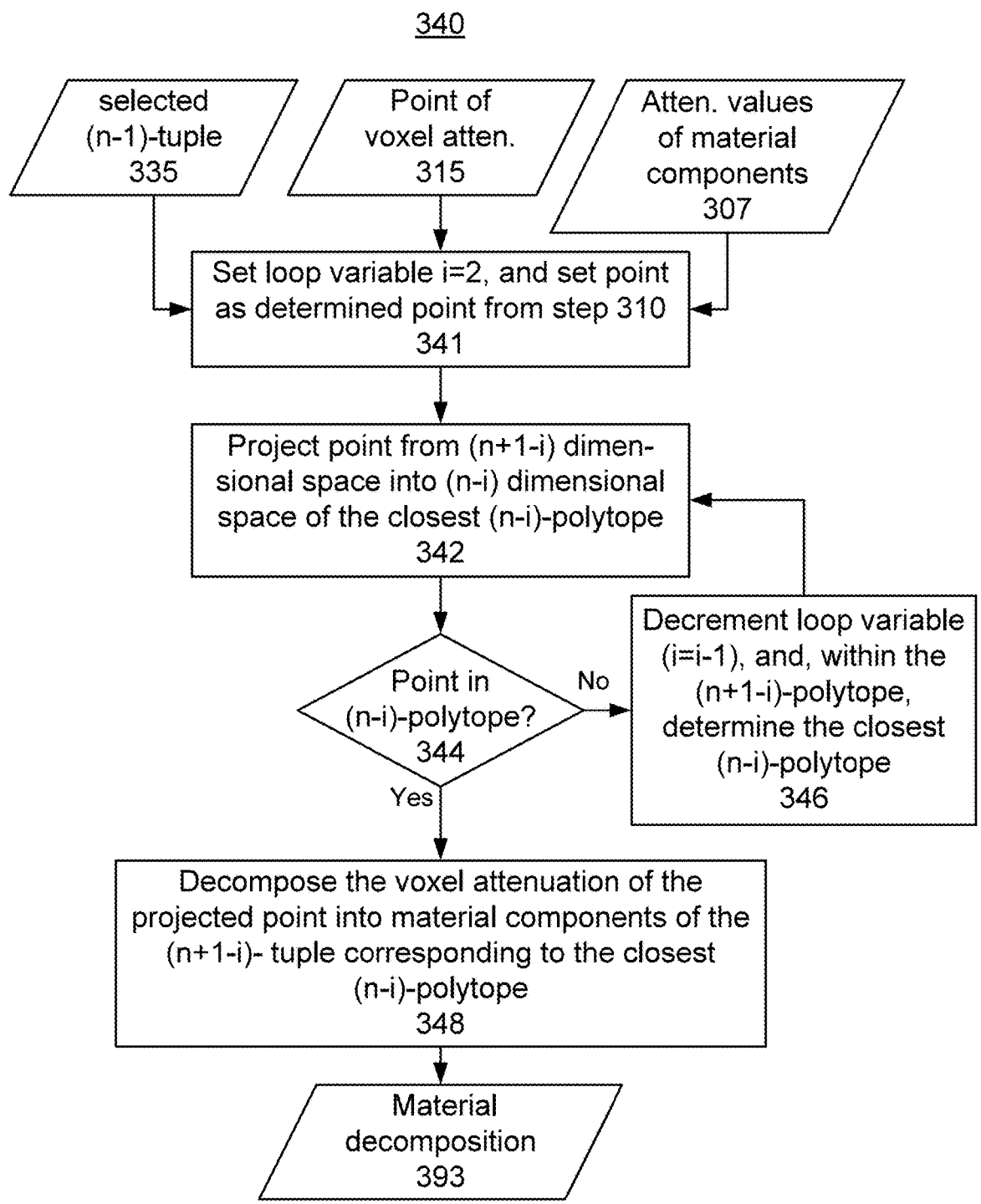
FIG. 3E shows a flow diagram of step 340 for decomposing attenuation values of a voxel into a selected (n-1)-tuple of material components of the closest (n-2)-polytope, according to one implementation.

FIG. 3E illustrates a flow diagram for step 340. As discussed above with reference to FIGS. 4B and 4C, when the point $\delta$ is not within a triangle, a series of orthogonal projections onto the reduced dimensional space of the closest polytope will eventual achieve the result that the projected point will be within the triangle, and the material decomposition can be performed once this is achieved. For example, in FIG. 4B, projecting the point $\delta$ onto the one-dimensional space of the line segment $\overline{\alpha\gamma}$ was sufficient to result in the point $\varepsilon$ being within the triangle. However, in FIG. 4C, two projections (i.e., a first projection onto the one-dimensional space of the line segment $\overline{\alpha\gamma}$ and a second projection of the projected point $\varepsilon$ onto the zero-dimensional space of the vertex $\gamma$) were required to achieve the result that the projected point $\zeta$ is within the triangle.

This process can generalize to the case when n=4, and rather than starting with evaluating whether the point $\delta$ is within a closest triangle, the initial inquiry is whether the point $\delta$ is within a closest triangular pyramid (i.e., a 3-polytope). Then, if the point $\delta$ is not within a closest triangular pyramid, the point $\delta$ is projected onto a two-dimensional space of the closest triangle. If the projected point onto the two-dimensional space is not within the closest triangle the process continues to reduced dimension as in the case when n=3, discussed above.

In FIG. 3E, this process is generalized to an arbitrary value of n. In step 341, the loop variable i is initialized to the value of two, and the point within the (n-1) dimensional space of the n-polytope is set to be the point $\delta$, which was determined in step 310.

In step 342, the point from the (n+1-i) dimensional space is projected onto a (n-i) dimensional space of a closest (n-i) polytope.

In step 344, an inquiry is performed regarding whether the projected point onto the (n-i) dimensional space is within the closest (n-i) polytope. If not, the loop continues to step 346. Otherwise, the loop proceeds to step 348.

In step 346, the loop variable i is decremented by one (i.e., i=i-1), and the closest (n-i) polytope to the projected onto the (n-i) dimensional space is determined. After step 346, the loop continues to step 342.

In step 348, the multi-material decomposition is performed to decompose the projected point into material components corresponding to the closest (n-i) polytope.

Figure 4D:
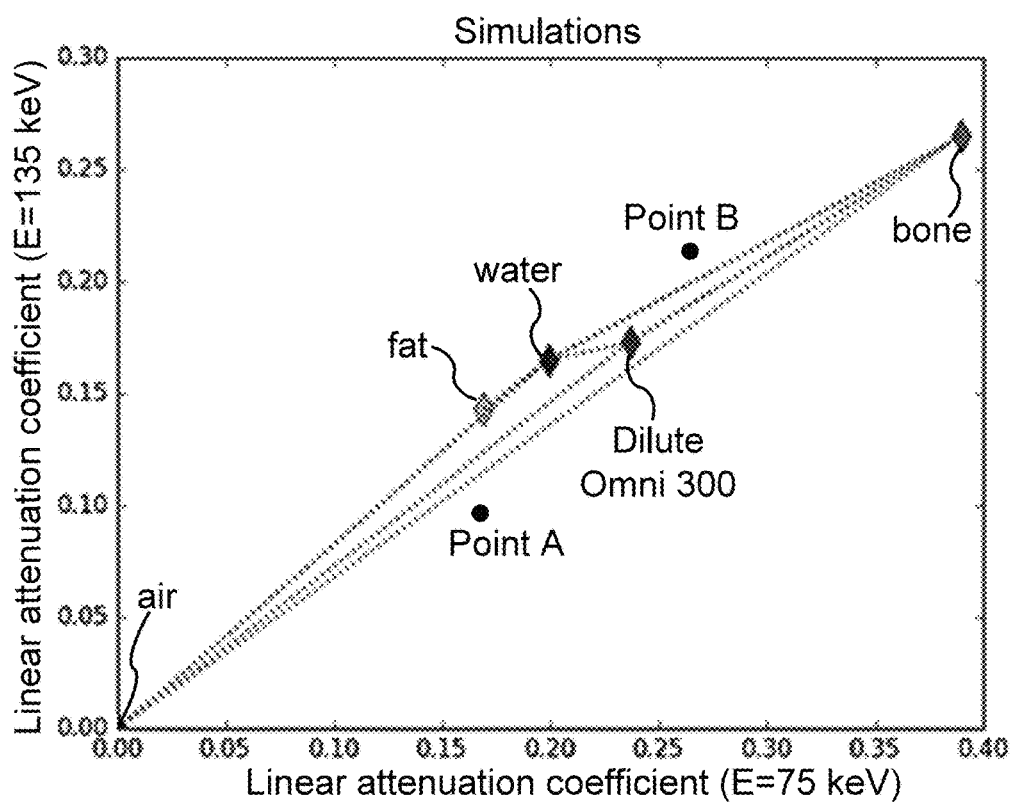
FIG. 4D shows a plot of multi-material decomposition with respect to triads of five material components, according to one implementation.

FIG. 4D illustrates a case in which five material components are considered. When the attenuation values for a first voxel are mapped to the point B shown in FIG. 4D, the point is not within any of the triangles of the respective triads of the material components.

According to the first method (e.g., the smallest Hausdorff distance approach) that determines the closest triangle using the Hausdorff distance, the triad of water, dilute Omni 300 (contrast agent), and bone correspond to the closest triangle.

Within this triangle, the closest edge corresponds to the pair of water and bone. Accordingly, the point B would be decomposed into a superposition of volume fractions of water and bone.

According to the second method (e.g., the closest edge approach) that determines the closest edge without first determining the closest triangle, the closest edge corresponds to the pair of water and bone. Accordingly, the material decomposition would be the same as with the first method.

When the attenuation values for a second voxel are mapped to the point A shown in FIG. 4D, the point is not within any of the triangles of the respective triads of the material components.

According to the first method that determines the closest triangle using the Hausdorff distance, the triad of air, fat, and dilute Omni 300 (contrast agent) correspond to the closest triangle. Within this triangle, the closest edge corresponds to the pair of air and dilute Omni 300. Accordingly, the point A would be decomposed into a superposition of volume fractions of air and dilute Omni 300.

According to the second method that determines the closest edge without first determining the closest triangle, the closest edge corresponds to the pair of air and bone. Accordingly, the point A would be decomposed into a superposition of volume fractions of air and bone, which is a different result from the first method.

Figure 5:
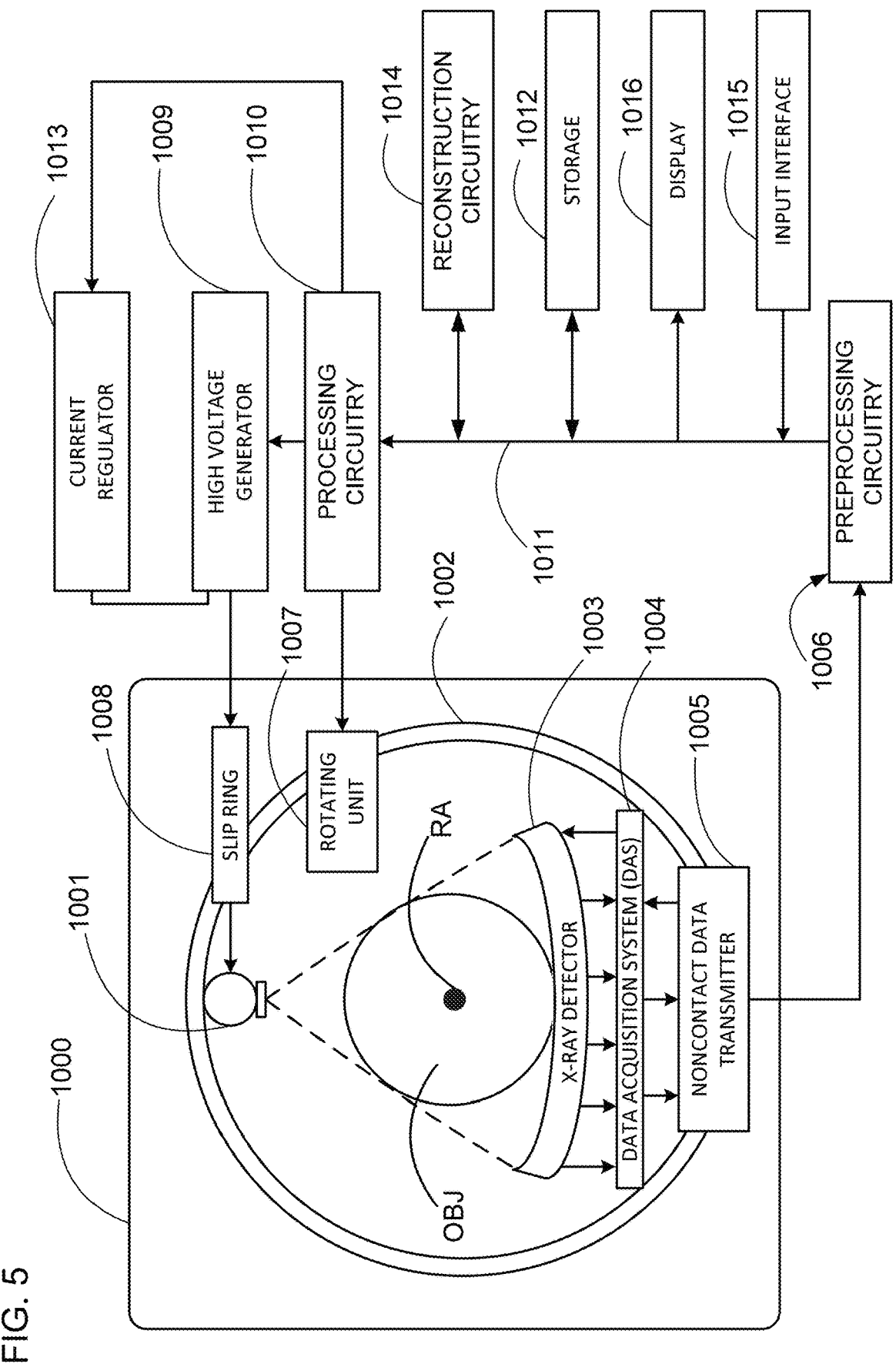
FIG. 5 shows a schematic of an implementation of a CT scanner using a third-generation geometry, according to one implementation.

FIG. 5 illustrates an implementation of the radiography gantry included in a CT apparatus or scanner. As shown in FIG. 5, a radiography gantry 1000 is illustrated from a side view and further includes an X-ray tube 1001, an annular frame 1002, and a multi-row or two-dimensional-array-type X-ray detector 1003. The X-ray tube 1001 and X-ray detector 1003 are diametrically mounted across an object OBJ on the annular frame 1002, which is rotatably supported around a rotation axis RA. A rotating unit 1007 rotates the annular frame 1002 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 1009 that generates a tube voltage applied to the X-ray tube 1001 through a slip ring 1008 so that the X-ray tube 1001 generates X-rays. The X-rays are emitted towards the object OBJ, whose cross sectional area is represented by a circle. For example, the X-ray tube 1001 having an average X-ray energy during a first scan that is less than an average X-ray energy during a second scan. Thus, two or more scans can be obtained corresponding to different X-ray energies. The X-ray detector 1003 is located at an opposite side from the X-ray tube 1001 across the object OBJ for detecting the emitted X-rays that have transmitted through the object OBJ. The X-ray detector 1003 further includes individual detector elements or units.

The CT apparatus further includes other devices for processing the detected signals from X-ray detector 1003. A data acquisition circuit or a Data Acquisition System (DAS) 1004 converts a signal output from the X-ray detector 1003 for each channel into a voltage signal, amplifies the signal, and further converts the signal into a digital signal. The X-ray detector 1003 and the DAS 1004 are configured to handle a predetermined total number of projections per rotation (TPPR).

The above-described data is sent to a preprocessing circuitry 1006, which is housed in a console outside the radiography gantry 1000 through a non-contact data transmitter 1005. The preprocessing circuitry 1006 performs certain corrections, such as sensitivity correction on the raw data. A storage 1012 stores the resultant data, which is also called projection data at a stage immediately before reconstruction processing. The storage 1012 is connected to a processing circuitry 1010 through a data/control bus 1011, together with a reconstruction device 1014, input interface 1015, and display 1016. The processing circuitry 1010 controls a current regulator 1013 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 1001 and the X-ray detector 1003 are diametrically mounted on the annular frame 1002 and are rotated around the object OBJ as the annular frame 1002 is rotated about the rotation axis RA. In the fourth-generation geometry system, the detectors are fixedly placed around the patient and an X-ray tube rotates around the patient. In an alternative embodiment, the radiography gantry 1000 has multiple detectors arranged on the annular frame 1002, which is supported by a C-arm and a stand.

The storage 1012 can store the measurement value representative of the irradiance of the X-rays at the X-ray detector unit 1003. Further, the storage 1012 can store a dedicated program for executing method 300.

The reconstruction circuitry 1014 can execute various steps of method 300. Further, reconstruction circuitry 1014 can execute pre-reconstruction processing image processing such as volume rendering processing and image difference processing as needed.

The pre-reconstruction processing of the projection data performed by the preprocessing circuitry 1006 can include correcting for detector calibrations, detector nonlinearities, and polar effects, for example.

Post-reconstruction processing performed by the reconstruction circuitry 1014 can include filtering and smoothing the image, volume rendering processing, and image difference processing as needed. The image reconstruction process can perform CT reconstruction to generate spectral images and implement various steps of method 300 on the spectral images. The reconstruction circuitry 1014 can use the memory to store, e.g., projection data, reconstructed images, calibration data and parameters, and computer programs.

The reconstruction circuitry 1014 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage 1012 can be non-volatile, such as ROM, EPROM, EEPROM or FLASH memory. The storage 1012 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction circuitry 1014 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 1016. The display 1016 can be an LCD display, CRT display, plasma display, OLED, LED or any other display known in the art.

The storage 1012 can be a hard disk drive, CD-ROM drive, DVD drive, FLASH drive, RAM, ROM or any other electronic storage known in the art.

Figure 6:
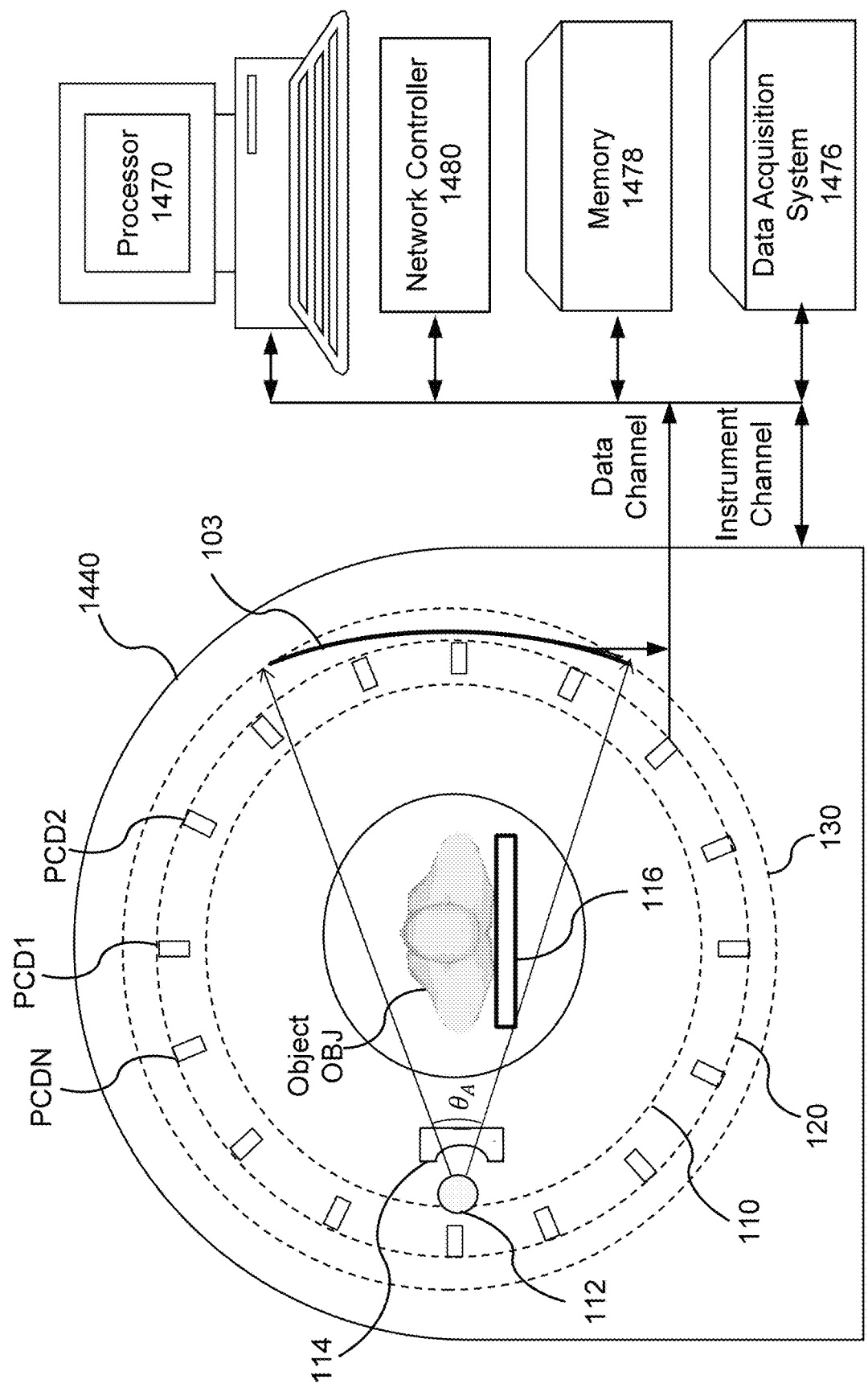
FIG. 6 shows a schematic of an implementation of a CT scanner using an energy-integrating detector array in a third-generation geometry and photon-counting detectors in a fourth-generation geometry, according to one implementation.

FIG. 6 shows another implementation of a computed tomography (CT) scanner having both energy-integrating detectors arranged in a third-generation geometry and PCDs arranged in a fourth-generation geometry. Illustrated in FIG. 6 is an implementation for placing the PCDs in a predetermined fourth-generation geometry in combination with a detector unit 103 in a predetermined third-generation geometry in a CT scanner system. The diagram illustrates relative positions among the X-ray source 112, the collimator/filter 114, the X-ray detector 103, and the photon-counting detectors PCD1 through PCDN.

In addition to the configuration of the X-ray source 112 and the detectors including the detector unit 103 and the PCDS show in FIG. 12, other types and combinations of X-ray detectors and X-ray source can be used to obtain the projection data. For example, either the detector unit 103 or the PCDS could be omitted from the scanner shown in FIG. 6 and the scanner could still obtain projection data, albeit different from the projection data obtained using the complete system shown in FIG. 12. Further, kV switching could be used with energy-integrating detectors or PCDs. In certain implementations, the PCDS can be direct X-ray detectors using semiconductors to convert the X-rays directly to photoelectrons without first generating scintillation photons. Additionally, in certain implementations, a broadband X-ray source can be used with spectrally-resolving X-ray detectors. These spectrally-resolving X-ray detectors can include PCDs in any configurations (e.g., a predetermined third-generation geometry or a predetermined fourth-generation geometry) or energy-integrating detectors preceded by respective spectral filters. In certain implementations, the X-ray source can include multiple narrow-band X-ray sources, such as in a dual source CT scanner. In general, any known combination of detector type and configuration together with any known type or combination of X-ray sources can be used to generate the projection data.

Returning to FIG. 12, FIG. 12 also shows circuitry and hardware for acquiring, storing, processing, and distributing X-ray projection data. The circuitry and hardware include: a processor 1470, a network controller 1480, a memory 1478, and a data acquisition system 1476.

In one alternative implementation, the CT scanner includes PCDs but does not include the energy-integrating detector unit 103.

As the X-ray source 112 and the detector unit 103 are housed in a gantry 1440 and rotate around circular paths 110 and 130 respectively, the photon-counting detectors PCDs and the detector unit 103 respectively detects the transmitted X-ray radiation during data acquisition. The photon-counting detectors PCD1 through PCDN intermittently detect the X-ray radiation that has been transmitted and individually output a count value representing a number of photons, for each of the predetermined energy bins. On the other hand, the detector elements in the detector unit 103 continuously detect the X-ray radiation that has been transmitted and output the detected signals as the detector unit 103 rotates. In one implementation, the detector unit 103 has densely placed energy-integrating detectors in predetermined channel and segment directions on the detector unit surface.

In one implementation, the X-ray source 112, the PCDs and the detector unit 103 collectively form three predetermined circular paths that differ in radius. At least one X-ray source 112 rotates along a first circular path 110 while the photon-counting detectors are sparsely placed along a second circular path 120. Further, the detector unit 103 travels along a third circular path 130. The first circular path 110, second circular path 120, and third circular path 130 can be determined by annular rings that are rotatably mounted to the gantry 1440.

Additionally, alternative embodiments can be used for placing the photon-counting detectors in a predetermined fourth-generation geometry in combination with the detector unit in a predetermined third-generation geometry in the CT scanner.

In one implementation, the X-ray source 112 is optionally a single energy source. In another implementation, the X-ray source 112 is configured to perform a kV-switching function for emitting X-ray radiation at a predetermined high-level energy and at a predetermined low-level energy. In still another alternative embodiment, the X-ray source 112 is a single source emitting a broad spectrum of X-ray energies. In still another embodiment, the X-ray source 112 includes multiple X-ray emitters with each emitter being spatially and spectrally distinct.

The detector unit 103 can use energy integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline, an organic liquid, a plastic, or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs).

The CT scanner also includes a data channel that routes projection measurement results from the photon-counting detectors and the detector unit 103 to a data acquisition system 1476, a processor 1470, memory 1478, network controller 1480. The data acquisition system 1476 controls the acquisition, digitization, and routing of projection data from the detectors. The data acquisition system 1476 also includes radiography control circuitry to control the rotation of the annular rotating frames 110 and 130. In one implementation data acquisition system 1476 will also control the movement of the bed 116, the operation of the X-ray source 112, and the operation of the X-ray detectors 103. The data acquisition system 1476 can be a centralized system or alternatively it can be a distributed system. In an implementation, the data acquisition system 1476 is integrated with the processor 1470. The processor 1470 performs functions including reconstructing images from the projection data, pre-reconstruction processing of the projection data, and post-reconstruction processing of the image data. The processor 1470 also performs the functions and methods described herein.

The pre-reconstruction processing of the projection data can include correcting for detector calibrations, detector nonlinearities, polar effects, noise balancing, and material decomposition.

The image-reconstruction process can be performed using filtered back-projection, iterative-image-reconstruction methods, or stochastic-image-reconstruction methods. Additionally, the reconstruction process can include various steps of method 300.

Post-reconstruction processing can include filtering and smoothing the image, volume rendering processing, and image difference processing as needed. Additionally, the Post-reconstruction processing can include various steps of method 300.

Both the processor 1470 and the data acquisition system 1476 can make use of the memory 1476 to store, e.g., projection data, reconstructed images, calibration data and parameters, and computer programs.

The processor 1470 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 1478 can be a hard disk drive, CD-ROM drive, DVD drive, FLASH drive, RAM, ROM or any other electronic storage known in the art.

The network controller 1480, such as an Intel Ethernet PRO network interface card from Intel Corporation of America, can interface between the various parts of the CT scanner. Additionally, the network controller 1480 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
circuitry configured to
obtain images corresponding to respective energy components, and
perform a material decomposition on the images to decompose attenuation values for the respective energy components of a voxel of the images into material components, wherein,
to perform the material decomposition, the circuitry is further configured to
determine whether the attenuation values of the voxel are consistent with a volume-fraction condition,
when the attenuation values of the voxel are consistent with the volume-fraction condition, decompose the attenuation values into n material components, wherein n is a natural number of three or greater, and,
when the attenuation values of the voxel are not consistent with the volume-fraction condition, project the attenuation values of the voxel onto a closest (n-2) dimensional space of n-1 material components to the attenuation values of the voxel to generate a projected point, and decompose attenuation values of the projected point into the n-1 material components.

2. The apparatus according to claim 1, wherein
the volume-fraction condition is that (i) volume fractions of the material components in the voxel are non-negative and (ii) a sum of the volume fractions for the voxel is one, and,
to determine whether the attenuation values of the voxel are consistent with the volume-fraction condition, the circuitry is further configured to
determine a point in an attenuation-energy space having coordinates given by the attenuation values of the voxel, the attenuation-energy space representing, along respective axes, attenuation values corresponding to respective components of the plurality of energy components, select an n-tuple by comparing the determined point with respective (n-1)-polytopes of n-tuples of a plurality of tuples, wherein an (n-1)-polytope of a given n-tuple has vertices corresponding respectively to n material components in the given n-tuple, each vertex of the (n-1)-polytope having coordinates of attenuation values of a unit volume fraction of a corresponding material component of the given n-tuple, when the determined point is within the (n-1)-polytope of the selected n-tuple, apply a Mendonça method to determine volume fractions of the n material components in the selected n-tuple as the material decomposition of the voxel, and, when the determined point is not within the selected (n-1)-polytope, determine a closest (n-2)-polytope of the (n-1)-polytope of the selected n-tuple that is closest to the determined point, and decompose the attenuation values of the voxel into volume fractions of material components of an (n-1)-tuple corresponding to the closest (n-2)-polytope.

3. The apparatus according to claim 2, wherein selecting the n-tuple by comparing the determined point with the respective (n-1)-polytopes is performed by the circuitry being further configured to select the selected n-tuple by comparing Hausdorff distances between the determined point and the respective (n-1)-polytopes and selecting, as the selected n-tuple, an n-tuple corresponding to a smallest Hausdorff distance between the determined point and the corresponding (n-1)-polytope.

4. The apparatus according to claim 2, wherein selecting the n-tuple by comparing the determined point with the respective (n-1)-polytopes is performed by the circuitry being further configured to select the selected n-tuple by determining a (n-1)-polytope that either (i) includes the determined point or, if none of the respective (n-1)-polytopes includes the determined point, (ii) includes a point within the respective (n-1)-polytopes that is closest to the determined point.

5. The apparatus according to claim 4, wherein, if multiple (n-1)-polytopes of the respective (n-1)-polytopes either includes the determined point or includes the point that is closest to the determined point, the selected n-tuple corresponds to a smallest (n-1)-polytopes of the multiple (n-1)-polytopes.

6. The apparatus according to claim 1, wherein the volume-fraction condition is that (i) volume fractions of the material components in the voxel are non-negative and (ii) a sum of the volume fractions for the voxel is one, and, to determine whether the attenuation values of the voxel are consistent with the volume-fraction condition, the circuitry is further configured to determine a point in an attenuation-energy space having coordinates given by the attenuation values of the voxel, the attenuation-energy space representing, along respective axes, attenuation values corresponding to respective components of the plurality of energy components, determine whether the determined point is within an enclosed region defined by a union of respective (n-1)-polytopes in the attenuation-energy space corresponding to respective n-tuples of material components, wherein an (n-1)-polytope of a given n-tuple has vertices corresponding to respective material components in the given n-tuple, a respective vertex of the (n-1)-polytope having coordinates of attenuation values of a unit volume fraction of a corresponding material component of the given n-tuple, when the determined point is within the enclosed region, apply a Mendonça method to determine volume fractions of the n material components in a selected n-tuple that corresponds to an (n-1)-polytope of the respective (n-1)-polytopes that is closest to the determined point, and, when the determined point is not within the enclosed region, determine a closest (n-2)-polytope within the respective (n-1)-polytopes that is closest to the determined point, and decompose the attenuation values of the voxel into volume fractions of material components of an (n-1)-tuple corresponding to the closest (n-2)-polytope.

7. The apparatus according to claim 2, wherein the projected point is an orthogonal projection of the determined point onto a (n-2)-dimensional space of the closest (n-2)-polytope, and, the circuitry is further configured to, when the determined point is not within the (n-1)-polytope of the selected n-tuple and the projected point is not within the closest (n-2)-polytope, determine a closest (n-3)-polytope to the determined point, the closest (n-3)-polytope being a (n-3)-polytope within the closest (n-2)-polytope that is closest to the determined point, and decompose the attenuation values of the voxel into volume fractions of (n-2) material components corresponding to the closest (n-3)-polytope.

8. The apparatus according to claim 6, wherein the projected point is an orthogonal projection of the determined point onto a (n-2)-dimensional space of the closest (n-2)-polytope, and, when the determined point is not within the enclosed region and the projected point is not within the closest (n-2)-polytope, the circuitry is further configured to determine a closest (n-3)-polytope to the determined point, the closest (n-3)-polytope being a (n-3)-polytope within the closest (n-2)-polytope that is closest to the determined point, and decompose the attenuation values of the voxel into volume fractions of (n-2) material components corresponding to the closest (n-3)-polytope.

9. The apparatus according to claim 2, wherein n is three or four, when n is four, the (n-1)-polytopes are triangles, the (n-2)-polytope is an edge, the selected n-tuple is a triad of the material components, and the determined (n-1)-tuple is a pair of the material components, and, when n is four, the (n-1)-polytopes are triangular pyramids, the (n-2)-polytope is a triangle, the selected n-tuple is a tetrad of the material components, and the determined (n-1)-tuple is a triad of the material components.

10. The apparatus according to claim 1, wherein, to obtain the images, the circuitry is configured to acquire projection data corresponding to the energy components for each detector element of a plurality of detector elements, the energy components representing radiation detected at the plurality of detector elements, and perform computed tomography on the projection data, reconstructing the images, each of the images corresponding to one of the respective energy components.

11. An apparatus, comprising:
an X-ray source configured to transmit X-rays;
a plurality of detector elements, wherein the plurality of detector elements is configured to
  detect a plurality of energy components of the X-rays, which are transmitted from the X-ray source through an object and are detected at the plurality of detector elements, and
  generate projection data having a plurality of energy components for each detector element of the plurality of detector elements, the energy components representing radiation of a respective energy profile; and
circuitry configured to
  reconstruct images for the projection data, each of the images corresponding to a respective component of the plurality of energy components,
  perform a material decomposition on the images to decompose attenuation values for the respective energy components of a voxel of the images into material components, wherein,
to perform the material decomposition, the circuitry is further configured to
  determine whether the attenuation values of the voxel are consistent with a volume-fraction condition,
  when the attenuation values of the voxel are consistent with the volume-fraction condition, decompose the attenuation values into n material components, wherein n is a natural number of three or greater, and,
  when the attenuation values of the voxel are not consistent with the volume-fraction condition, project the attenuation values of the voxel onto a closest (n-2) dimensional space of n-1 material components to the attenuation values of the voxel to generate a projected point, and decompose attenuation values of the projected point into the n-1 material components.

12. A method, comprising:
obtaining images corresponding to respective energy components, and
performing a material decomposition on the images to decompose attenuation values for the respective energy components of a voxel of the images into material components, wherein the material decomposition includes
  determining whether the attenuation values of the voxel are consistent with a volume-fraction condition,
  when the attenuation values of the voxel are consistent with the volume-fraction condition, decomposing the attenuation values into n material components, wherein n is a natural number of three or greater, and,
  when the attenuation values of the voxel are not consistent with the volume-fraction condition, projecting the attenuation values of the voxel onto a closest (n-2) dimensional space of n-1 material components to the attenuation values of the voxel to generate a projected point, and decomposing attenuation values of the projected point into the n-1 material components.

13. The method according to claim 12, wherein
the volume-fraction condition is that (i) volume fractions of the material components in the voxel are non-negative and (ii) a sum of the volume fractions for the voxel is one, and
the step of determining whether the attenuation values of the voxel are consistent with the volume-fraction condition further comprises
  determining a point in an attenuation-energy space having coordinates given by the attenuation values of the voxel, the attenuation-energy space representing, along respective axes, attenuation values corresponding to respective components of the plurality of energy components,
  selecting an n-tuple by comparing the determined point with respective (n-1)-polytopes of n-tuples of a plurality of tuples, wherein an (n-1)-polytope of a given n-tuple has vertices corresponding respectively to n material components in the given n-tuple, each vertex of the (n-1)-polytope having coordinates of attenuation values of a unit volume fraction of a corresponding material component of the given n-tuple,
  when the determined point is within the selected (n-1)-polytope, applying a Mendonça method to determine volume fractions of the n material components in the selected n-tuple as the material decomposition of the voxel, and,
  when the determined point is not within the selected (n-1)-polytope, determining a closest (n-2)-polytope of the (n-1)-polytope of the selected n-tuple that is closest to the determined point, and decomposing the attenuation values of the voxel into volume fractions of material components of an (n-1)-tuple corresponding to the closest (n-2)-polytope.

14. The method according to claim 13, wherein selecting the n-tuple further comprises comparing Hausdorff distances between the determined point and the respective (n-1)-polytopes and selecting, as the selected n-tuple, an n-tuple corresponding to a smallest Hausdorff distance between the determined point and the corresponding (n-1)-polytope.

15. The method according to claim 12, wherein selecting the n-tuple further comprises comparing the determined point with the respective (n-1)-polytopes is performed by the circuitry being further configured to select the selected n-tuple by determining a (n-1)-polytope that either (i) includes the determined point or, if none of the respective (n-1)-polytopes includes the determined point, (ii) includes a point within the respective (n-1)-polytopes that is closest to the determined point.

16. The method according to claim 12, wherein
the volume-fraction condition is that (i) volume fractions of the material components in the voxel are non-negative and (ii) a sum of the volume fractions for the voxel is one, and
the step of determining whether the attenuation values of the voxel are consistent with the volume-fraction condition further comprises
  determining a point in an attenuation-energy space having coordinates given by the attenuation values of the voxel, the attenuation-energy space representing, along respective axes, attenuation values corresponding to respective components of the plurality of energy components,
  determining whether the determined point is within an enclosed region defined by a union of respective (n-1)-polytopes in the attenuation-energy space corresponding to respective n-tuples of material components, wherein an (n-1)-polytope of a given n-tuple has vertices corresponding to respective material components in the given n-tuple, a respective vertex of the (n-1)-polytope having coordinates of attenuation values of a unit volume fraction of a corresponding material component of the given n-tuple, when the determined point is within the enclosed region, applying a Mendonça method to determine volume fractions of the n material components in a selected n-tuple that corresponds to an (n-1)-polytope of the respective (n-1)-polytopes that is closest to the determined point, and, when the determined point is not within the enclosed region, determining a closest (n-2)-polytope within the respective (n-1)-polytopes that is closest to the determined point, and decomposing the attenuation values of the voxel into volume fractions of material components of an (n-1)-tuple corresponding to the closest (n-2)-polytope.

17. The method according to claim 16, wherein
the projected point is an orthogonal projection of the determined point onto a (n-2)-dimensional space of the closest (n-2)-polytope, and the method further comprises, when the determined point is not within the enclosed region and the projected point is not within the closest (n-2)-polytope, determining a closest (n-3)-polytope to the determined point, the closest (n-3)-polytope being a (n-3)-polytope within the closest (n-2)-polytope that is closest to the determined point, and decomposing the attenuation values of the voxel into volume fractions of (n-2) material components corresponding to the closest (n-3)-polytope.

18. The method according to claim 13, wherein
the projected point is an orthogonal projection of the determined point onto a (n-2)-dimensional space of the closest (n-2)-polytope, and the method further comprises, when the determined point is not within the (n-1)-polytope of the selected n-tuple and the projected point is not within the closest (n-2)-polytope, determining a closest (n-3)-polytope to the determined point, the closest (n-3)-polytope being a (n-3)-polytope within the closest (n-2)-polytope that is closest to the determined point, and decomposing the attenuation values of the voxel into volume fractions of (n-2) material components corresponding to the closest (n-3)-polytope.

19. The method according to claim 12, wherein the step of obtaining the images further comprises acquiring projection data corresponding to the energy components for each detector element of a plurality of detector elements, the energy components representing radiation detected at the plurality of detector elements, and performing computed tomography on the projection data, reconstructing the images, each of the images corresponding to one of the respective energy components.

20. A non-transitory computer readable storage medium including executable instruction, wherein the instructions, when executed by circuitry, cause the circuitry to perform the method according to claim 12.

* * * * *